United States Patent
Schneider

(10) Patent No.: US 6,377,348 B1
(45) Date of Patent: Apr. 23, 2002

(54) SMOKE CHAMBER FOR EVALUATING FOUNDRY SAND SHAPES AND ITS METHOD OF USE

(75) Inventor: James Thurston Schneider, Dublin, OH (US)

(73) Assignee: Ashland, Inc., Covington, KY (US)

( * ) Notice: Subject to any disclaimer, the term of this patent is extended or adjusted under 35 U.S.C. 154(b) by 20 days.

(21) Appl. No.: 09/633,395

(22) Filed: Aug. 7, 2000

(51) Int. Cl.[7] .................. G01N 21/53; G01N 21/59; G01N 25/00
(52) U.S. Cl. ................. 356/439; 250/573; 374/8
(58) Field of Search ................. 356/439, 438, 356/437; 250/343, 373, 573; 374/8

(56) References Cited

U.S. PATENT DOCUMENTS

| | | | | |
|---|---|---|---|---|
| 3,662,586 A | * | 5/1972 | Suga | 374/8 |
| 3,867,640 A | * | 2/1975 | Paulsen | 250/573 |
| 4,637,735 A | * | 1/1987 | de Ris et al. | 374/8 |
| 5,009,591 A | * | 4/1991 | Watanabe | 432/128 |

* cited by examiner

Primary Examiner—F. L. Evans
Assistant Examiner—Zandra V. Smith
(74) Attorney, Agent, or Firm—Mueller and Smith, LPA

(57) ABSTRACT

A smoke chamber for determining the amount of visible smoke emitted by a foundry core/mold resin system is composed of an elongate chamber having a proximal end, a distal end, and sides. The chamber is fitted with air inlet at its proximal end, a smoke outlet at its distal end, and a sample station disposed between the air inlet and the smoke outlet. The sample station includes a sample holder and furnace for heating a sample placed in the sample holder. The chamber also includes a light assembly disposed along one side of the chamber from the sample station to the smoke outlet. A light detection assembly is disposed on a chamber side opposite the light assembly for detecting light emitted from the light assembly. The chamber also includes fan for drawing smoke from a heated sample placed in the sample holder to the smoke outlet. The corresponding method for determining the amount of visible smoke emitted by a foundry core/mold resin system includes placing a sample in the sample holder. The sample in the sample station is heated by the furnace to pyrolize the sample. The amount of visible smoke emitted by the pyrolized sample is measured with the light detection assembly. Desirably, the light detection assembly is composed of a plurality of discrete photodetection units, each of which is in. electrical connection with a recorder for recording the amount of visible light detected by each of the photodetection units.

12 Claims, 3 Drawing Sheets

SMOKE CHAMBER FOR EVALUATING FOUNDRY SAND SHAPES AND ITS METHOD OF USE

CROSS-REFERENCE TO RELATED APPLICATIONS

None

STATEMENT REGARDING FEDERALLY SPONSORED RESEARCH

Not applicable.

BACKGROUND OF THE INVENTION

The present invention relates generally to casting metals and more particularly to the foundry core/resin shapes wherein the resinous binder and some additives emit smoke during metal casting operations.

Commercial foundries have trouble regulating the amount of visible smoke emitted from cured core/mold packages when molten ferrous or non-ferrous metals are poured into the shapes. The molten metals cause the aggregate mixes, containing a variety of common foundry resin compositions, to burn. Such mixes emit a quantity of smoke, either from the burning of the resin components, water vapor, release agents, refractory coatings, or other compounds and/or additives used in the core/mold making process. Reduction of such smoke is desirable from the foundry's standpoint, both environmentally as well as for worker health and/or safety.

Heretofore, however, foundries have not had the tools necessary for them to evaluate various foundry binder systems in a controlled or laboratory-type environment in order to adjudge the ones that emit less visible smoke at the metal pouring areas. The present invention is addressed to such need in the foundry art.

BRIEF SUMMARY OF THE INVENTION

A smoke chamber for determining the amount of visible smoke emitted by a foundry core/mold resin system is composed of an elongate chamber having a proximal end, a distal end, and sides. The chamber is fitted with air inlet at its proximal end, a smoke outlet at its distal end, and a sample station disposed between the air inlet and the smoke outlet. The sample station includes a sample holder and furnace (either external or internal) for heating a sample placed in the sample holder. The chamber also includes a light assembly disposed along one side of the chamber from the sample station to the smoke outlet. A light detection assembly is disposed on a chamber side opposite the light assembly for detecting light emitted from the light assembly. The chamber may be covered or darkened in order to exclude extraneous light, which might be detected by the light detection assembly. The chamber also includes fan for drawing smoke from a heated sample placed in the sample holder to the smoke outlet. For present purposes, a "foundry core/mold resin system" includes resin components, water, release agents, refractory coatings, or other compounds, and/or additives, and aggregate used in the core/mold making process. While the inventive smoke chamber can be used to evaluate resin compositions alone, preferably the actual commercial system (resin, aggregate, and additives) will be evaluated.

The corresponding method for determining the amount of visible smoke emitted by a foundry core/mold resin system includes placing a sample in the sample holder. The sample in the sample station is heated by the furnace to pyrolize the sample. The amount of visible smoke emitted by the pyrolized sample is measured with the light detection assembly. Desirably, the light detection assembly is composed of a plurality of discrete photodetection units, each of which is in electrical connection with a recorder for recording the amount of visible light detected by each of the photodetection units. In this way, different foundry core/mold resin systems can be evaluated and compared to determine which foundry core/mold resin system has the characteristics desired for any particular use.

BRIEF DESCRIPTION OF THE DRAWINGS

For a fuller understanding of the nature and objects of the present invention, reference should be had to the following detailed description taken in connection with the accompanying drawings in which.

The drawings will be described in detail below.

DETAILED DESCRIPTION OF THE INVENTION

By employing the novel smoke chamber, the foundry core/mold resin system designer can readily test such resin systems for the amount of visible smoke that is emitted during heating to foundry casting temperatures. This gives the resin system formulator/designer the ability to design and test new formulations designed to emit reduced amounts of visible smoke, which is desired by the foundry. Lowering emissions during casting operations is an environmental benefit as well as a worker benefit to the foundry.

Figure 1:
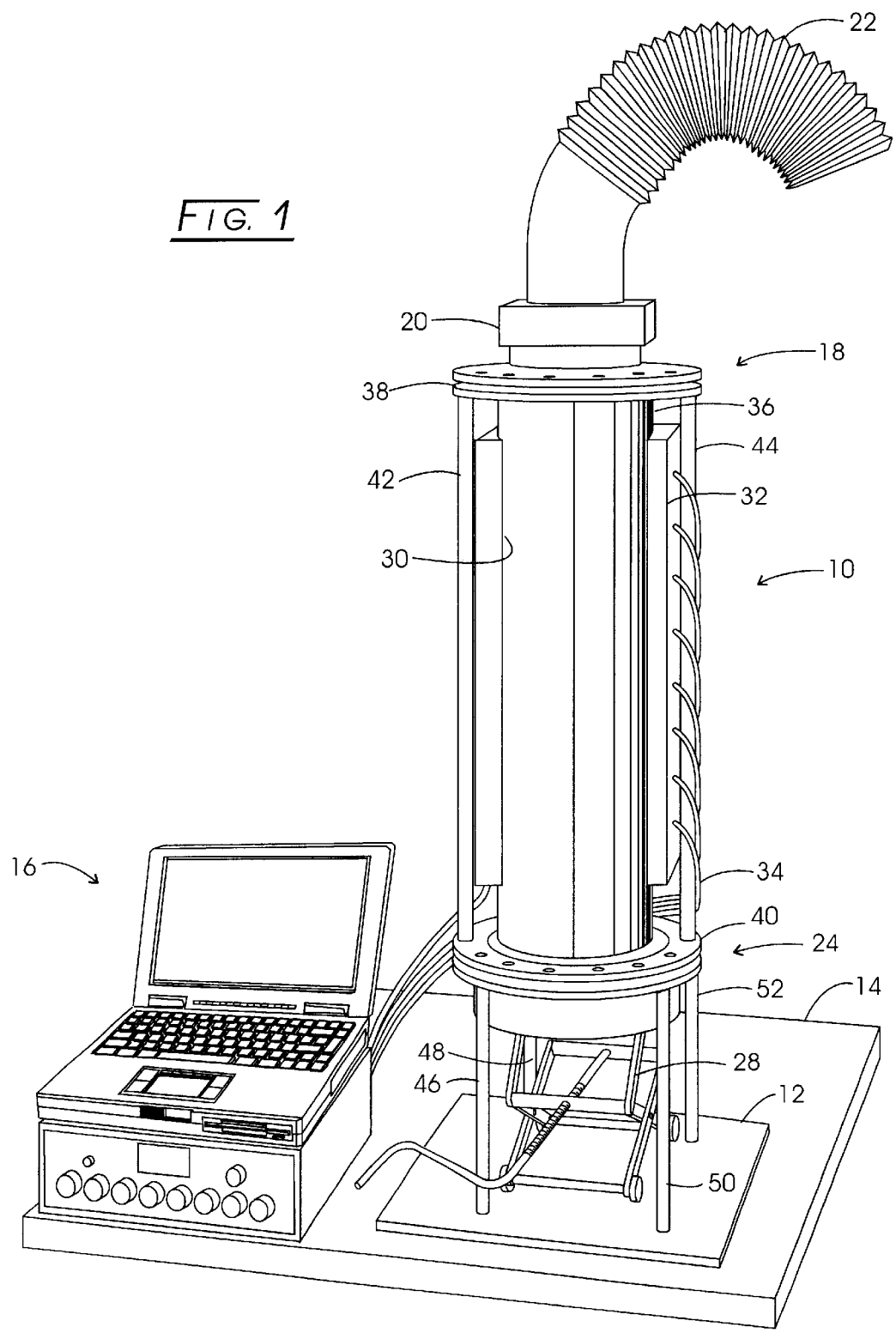
FIG. 1 is a perspective view of the smoke chamber interconnected to a personal computer for interpreting data generated by the smoke chamber.

Referring initially to FIG. 1, a smoke chamber, 10, is seen mounted on a base, 12, which in turn is mounted on a platform, 14. A data acquisition unit, preferably a computer, 16, also is mounted to platform 14 and is interconnected to photodetection units mounted on smoke chamber 10, as will be described in more detail in connection with FIG. 2. Smoke chamber 10 is seen to have an upper distal end, 18, fitted with a plenum chamber, 20, which is connected to a flexible hose, 22. Smoke chamber 10 also has a lower proximal end, 24, which locates a sample or testing station, 26, which may include a furnace and a sample cart, 28, which is movable from a loading station up to testing or sample station 26. Mounted vertically along one side of smoke chamber 10 is a light source, 30. Disposed opposite to light source 30 is a detector array, 32, which is in communication with computer 16 via a series of cable, such as cable 34a.

Smoke chamber 10 has a central elongate burn chamber, 36, which is disposed between an overhead distal flange set, 38, and a lower proximal flange set, 40, which flange sets are held together by a pair of oppositely-disposed rods, 42 and 44. Flange set 40 rests above base 10 on four legs, 46–52. The space created accommodates cart 28. All exterior surface areas of burn chamber 36, except along the face of light source 30 and the face of detector array 32, are coated or covered in a flat-black color to exclude any stray light from being detected by detector array 32.

Figure 2:
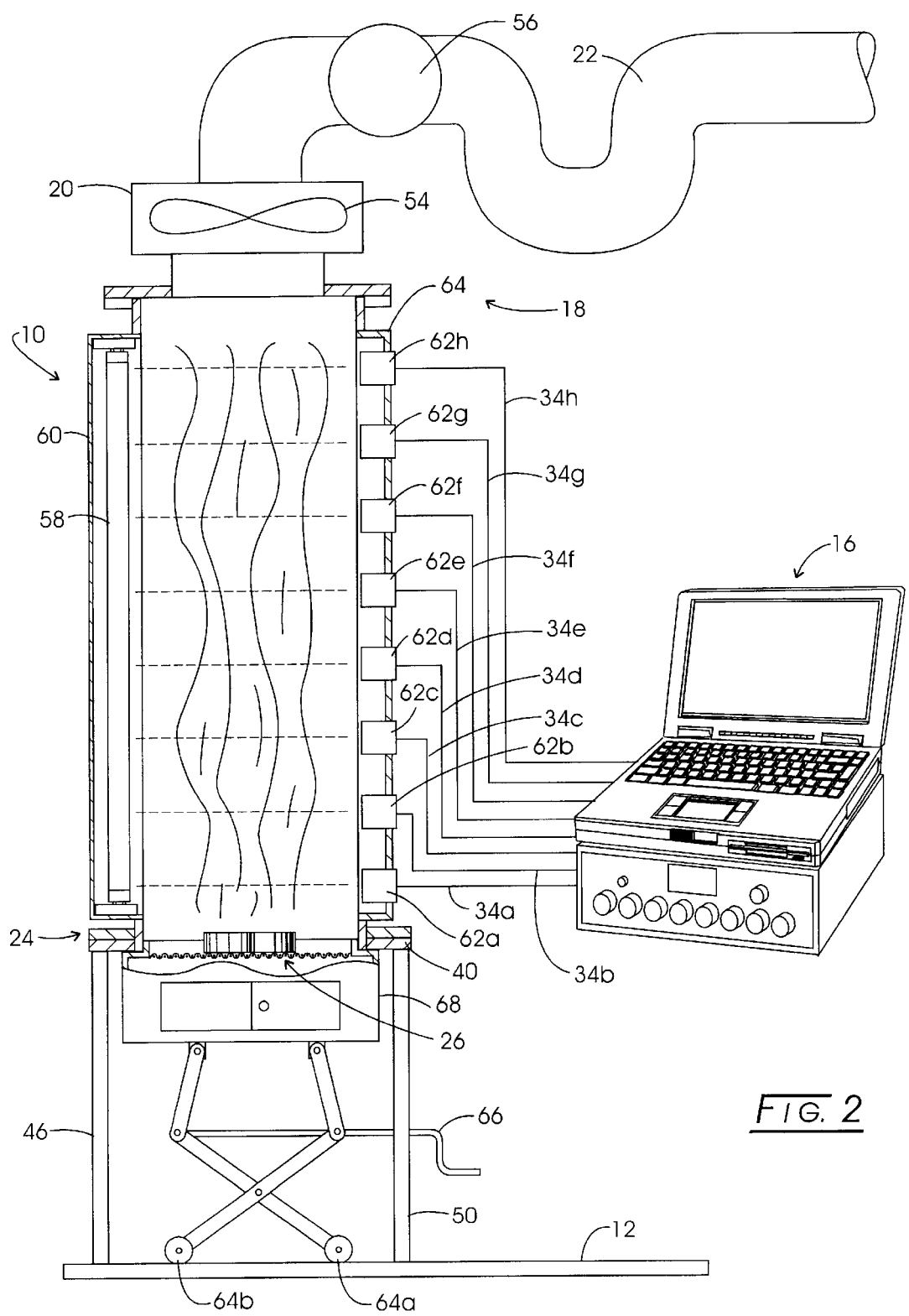
FIG. 2 is an elevational cross-section of the smoke chamber showing the connection of the photodetection units to the personal computer.

Referring to FIG. 2, it will be observed that plenum 20 houses a fan, 54, which draws air and smoke up through burn chamber 36 and exhausts such air/smoke mixture via hose 22. Disposed in hose 22 is a flow meter, 56, for measuring the amount of air being exhausted from burn chamber 36.

It will be observed that light source 30 is composed of a light tube, 58, and an outer protective cover, 60. Detector array 32 is seen to be composed of an array of photodetectors, 62a–62h, which are connected to computer 16 via cables, 34a–34h, respectively. Photodetectors 62a–62h are housed in a protective cover, 64.

Figure 3:
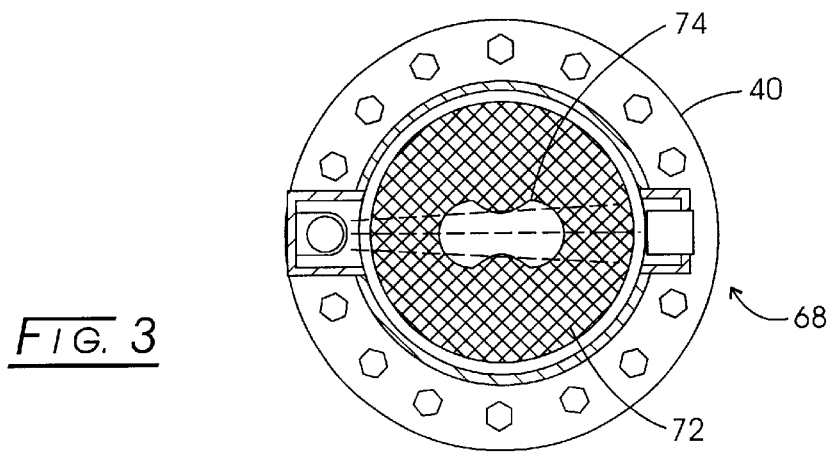
FIG. 3 is a plan view of the sample holder in the smoke chamber.
Figure 4:
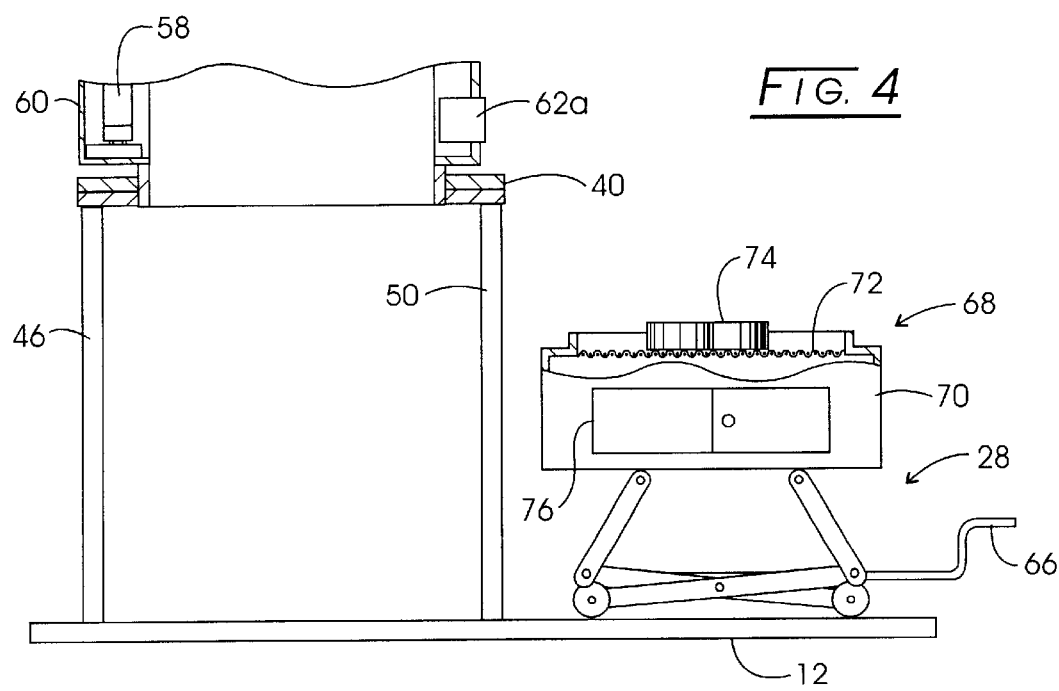
FIG. 4 is an enlarged side view of the sample cart in a rest position away from the smoke chamber.

Cart 28 is mounted on wheels, e.g., 64a and 64b, and can be raised (as seen in FIG. 2) and lowered (as seen in FIG. 4) via a scissors arrangement by a threaded crank, 66. Referring to FIGS. 3 and 4 also), atop the scissors mechanism is a specimen tray, 68, which consists of a lower sand collection box, 70, an upper screen, 72, for holding a specimen 74, which typically is a so-called dog bone specimen of resin and sand aggregate. From FIG. 4, it will be observed that cart 68 can be moved from a lowered position away from smoke chamber 10, to a position between legs 46–52 and underneath smoke chamber 10. By turning crank 66, specimen tray 68 can be raised up to the testing station 26. Air is admitted into burn chamber 36 via an air inlet, doors 76. If proximal end 24 includes a furnace, dog bone 74 can be pyrolized with unburned sand falling down through screen 72 into collection box 70. Such sand can be removed also via doors 76. In the drawings, furnace 10 was not fitted with an internal furnace, but instead relied on a separate stand-alone furnace to pyrolize dog bone 74, which then was immediately conveyed via cart 28 into position at testing station 26, as described above.

Smoke rising from the pyrolized dog bone proceeds up burn chamber 36, being drawn by fan 54. The intensity of light from tube 58 diminishes in response to smoke with a consequent diminution in the signal being sensed by photodetector array 32. The more smoke that is evolved from sample 74, the greater the attenuation of the signals being sensed by detector array 32. The signals from array 32 are sent to computer 16 for display to the operator via a visual display and/or printed display. Special algorithms can be evolved for use in computer 16 as is necessary, desirable, or convenient.

With more sensitive photodetectors installed in array 32, stray light entering burn chamber 36 can skew test results. Thus, hose 22 is bent to the side to ensure that stray light does not enter burn chamber 36 through the end of hose 22. Also, burn chamber 36 preferably should be made of light opaque material to suppress extraneous light from entering the chamber. Of course, chamber 36 adjacent tube 58 needs to be transparent to the light emitted by tube 58. Additionally, the number of photodetectors illustrated in the drawings is illustrative only, as a greater or lesser number can be used. Further, tube 58 can be replaced with additional light sources as is necessary, desirable, or convenient. Smoke exhausted via hose 22 optionally can be sent to pollution recovery systems and/or to an analyzer to analyze the composition of the smoke.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

What is claimed is:

1. A smoke chamber for determining the amount of visible smoke emitted by a foundry core/mold resin system, which comprises:
    an elongate chamber having a proximal end, a distal end, sides, and being fitted with:
    (a) air inlet at its proximal end;
    (b) a smoke outlet at its distal end;
    (c) a sample station disposed between said air inlet and said smoke outlet, and comprising a sample holder and furnace for heating a sample placed in said sample holder;
    (d) a light assembly disposed along one side of said chamber;
    (e) a light detection assembly disposed on a chamber side opposite said light assembly for detecting light emitted from said light assembly; and
    (f) a fan for drawing smoke from a heated sample placed in said sample holder to said smoke outlet.

2. The smoke chamber of claim 1, wherein said light assembly is disposed from adjacent said sample station to adjacent said smoke outlet.

3. The smoke chamber of claim 1, wherein said light detection assembly comprises photodetectors.

4. The smoke chamber of claim 1, wherein said fan is located at said smoke outlet.

5. The smoke chamber of claim 1, which further includes a cart which retains said sample holder, said cart being wheeled for its movement and being vertically adjustable for raising and lowering said sample holder.

6. The smoke chamber of claim 1, wherein said light detection assembly is connected to a data acquisition computer.

7. Method for determining the amount of visible smoke emitted by a foundry core/mold resin system, which comprises:
    (i) placing a sample of said core/mold resin system in a smoke chamber, which comprises:
        an elongate chamber having a proximal end, a distal end, sides, and being fitted with:
        (a) air inlet at its proximal end;
        (b) a smoke outlet at its distal end;
        (c) a sample station disposed between said air inlet and said smoke outlet, and comprising a sample holder and furnace for heating a sample placed in said sample holder;
        (d) a light assembly disposed along one side of said chamber from said sample station to said smoke outlet; and
        (e) a light detection assembly disposed on a chamber side opposite said light assembly for detecting light emitted from said light assembly;
    (ii) heating with the furnace said sample in said sample station to pyrolize said sample; and
    (iii) measuring with said light detection assembly the amount of visible smoke emitted by said pyrolized sample.

8. The method of claim 7, wherein said light assembly is disposed from adjacent said sample station to adjacent said smoke outlet.

9. The method of claim 7, wherein said light detection assembly comprises photodetectors.

10. The method of claim 7, wherein said fan is located at said smoke outlet for drawing said smoke from said sample station to said smoke outlet.

11. The method of claim 7, which further includes a cart which retains said sample holder, said cart being wheeled for its movement and being vertically adjustable for raising and lowering said sample holder.

12. The method of claim 7, wherein said light detection assembly is connected to a data acquisition computer.

* * * * *